United States Patent [19]
Keo et al.

[11] Patent Number: 5,599,433
[45] Date of Patent: Feb. 4, 1997

[54] CAPILLARY ELECTROPHORESIS OF GLYCOSYLATED PROTEINS

[75] Inventors: Nida Keo, Rialto; Zara Safarian, Brea; Cheng-Ming Liu; Hann-Ping Wang, both of Yorba Linda, all of Calif.

[73] Assignee: Beckman Instruments, Inc., Fullerton, Calif.

[21] Appl. No.: 373,680

[22] Filed: Jan. 17, 1995

[51] Int. Cl.$^6$ .................................................. C25B 7/00
[52] U.S. Cl. .................. 204/451; 204/452; 510/501; 510/465; 510/495
[58] Field of Search .................................. 252/135, 140, 252/545, 546; 204/180.1, 451, 452; 510/501, 465, 495

[56] References Cited

U.S. PATENT DOCUMENTS

| | | | |
|---|---|---|---|
| 3,852,213 | 12/1974 | Cooney | 252/181 |
| 4,209,372 | 6/1980 | Bluestein et al. | 204/180 G |
| 4,537,707 | 8/1985 | Severson, Jr. | 252/545 |
| 4,925,545 | 5/1990 | Murel | 204/182.9 |
| 5,120,413 | 6/1992 | Chen et al. | 204/180.1 |
| 5,139,630 | 8/1992 | Chen | 204/180.1 |
| 5,240,576 | 8/1993 | Lauer et al. | 204/180.1 |
| 5,259,939 | 11/1993 | Chen | 204/180.1 |
| 5,310,462 | 3/1994 | Chen | 204/180.1 |

FOREIGN PATENT DOCUMENTS

| | | |
|---|---|---|
| A-494686 | 7/1992 | European Pat. Off. |
| WO-A-9220717 | 11/1992 | WIPO |

OTHER PUBLICATIONS

CA 112: 194775.

"Use of Zwitterionic Buffer Additives to Improve the Separation of Proteins in Capillary Zone Electrophoresis", X. Fang, T. Zhu and V. Sun, Journal of High Resolution Chromatography, vol. 17, Nov. 1994.

International Search Report, PCT/US95/16940 May 30, 1996.

Bernstein, R. E., "Nonenzymatically Glycosylated Proteins," Advances in Clinical Chemistry, vol. 26, pp. 1–78, 1987.

Little, R. R. et al., "Interlaboratory Comparison of Glycohemoglobin Results," Clinical Chemistry, vol. 37, No. 10, pp. 1725–1729, 1991.

*Primary Examiner*—Howard E. Schain
*Assistant Examiner*—Cybille Delacroix-Muirheid
*Attorney, Agent, or Firm*—William H. May; Gary T. Hampson; Sheldon & Mak

[57] ABSTRACT

A buffer and method useful for the analysis of glycoproteins by capillary zone electrophoresis. The buffer comprises water, a sugar complexing compound, a base compound for adjusting the pH, and a zwitterionic compound. An embodiment of the buffer comprises sodium borate as the complexing compound, sodium hydroxide as the base, and 3-cyclohexylamino-1-propanesulfonic acid as the zwitterionic compound. In the method, a selected glycoprotein is subjected to capillary zone electrophoresis. The proportion or the amount of the glycoprotein is determined by quantitative analysis of the resulting electropherogram.

24 Claims, 2 Drawing Sheets

CAPILLARY ELECTROPHORESIS OF GLYCOSYLATED PROTEINS

RELATED APPLICATIONS

The present application is related to U.S. application Ser. No. 08/133,514, entitled "USE OF CAPILLARY ELECTROPHORESIS FOR QUANTITATION OF THE CONCENTRATION OF PROTEIN COMPONENT AND TOTAL PROTEIN IN HUMAN BODY FLUID", filed Oct. 7, 1993, by Hann-Ping Wang and Cheng-Ming Liu, and U.S. application Ser. No. 08/283,137, entitled "QUANTITATIVE ANALYSIS OF HEMOGLOBIN A1C BY IMMUNOCAPILLARY ELECTROPHORESIS", filed Jul. 29, 1994, by Hann-Ping Wang and Zara Safarian, all incorporate herein by reference.

BACKGROUND

The present application is directed to reagents and methods of capillary electrophoresis, which are suitable for measuring nonenzymatically glycosylated proteins in clinical specimens. These materials and methods are particularly useful for monitoring glycemic control in diabetics.

Assays for glycated hemoglobin have been performed in clinical laboratories for well over a decade. Analysis of normal hemoglobin, Hb A, has shown that it contains a number of minor hemoglobin species. These minor species, which have been designated Hb A1a, Hb A1b, and Hb A1c, are referred to as glycated hemoglobins or glycohemoglobins. They are formed by condensation of an amino group of hemoglobin with an aldehyde group of a reducing sugar. For Hb A1c, glycated hemoglobin is formed by the condensation of the N-terminal valine of the hemoglobin beta chain with glucose to form an unstable Schiff base or aldimine (also known as pre-A1c), which then undergoes an Amadori rearrangement to form a stable ketoamine.

The formation of glycated hemoglobin is nonenzymatic. It occurs over the lifespan of the red blood cell, which is about 120 days under normal conditions. The amount of glycated hemoglobin formed is also proportional to the concentration of glucose in the blood. Consequently, the concentration of Hb A1c in the blood is related to the time-averaged glucose concentration over the two or three month period prior to measurement. This value provides a way of measuring control of diabetes, where the results are not affected by short-term fluctuations in plasma glucose levels. Therefore, measurement of glycohemoglobins can complement other more traditional methods of assessing control of diabetes. For example, measurement of glycohemoglobins can be used to verify patient compliance, where self administered urine or blood glucose records may be falsified or blood glucose levels vary markedly throughout the day or from day to day. Other applications include new patients with known or suspected diabetes in whom there is no previous record of blood glucose concentration or during pregnancy when close control of diabetes is especially important.

Currently available methods for the determination of glycohemoglobin can be divided into two different categories. The first category includes methods, such as colorimetry, affinity chromatography, and immunoassay, that separate minor hemoglobin components based on the structural characteristics of sugar moieties on hemoglobin. The second category, which includes ion exchange chromatography, high-performance liquid chromatography, electrophoresis, and isoelectric focusing, separates hemoglobin components based on charge differences between glycosylated and nonglycosylated proteins. A comparison of these methods has been reported (Ralph E. Bernstein, "Nonenzymatically Glycosylated Proteins," *Advances in Clinical Chemistry*, Vol. 26, 1–78 (1987)).

A colorimetric method has been devised based on the observation that Hb A1c, when subject to mild acid hydrolysis, releases 5-hydroxymethylfurfural (5-HMF). This test has proven difficult to standardize because the yield of 5-HMF from Hb A1c is only about 30%. In order to provide reliable results, reaction conditions must be carefully controlled for inter alia temperature, pressure, and time. A further drawback is the use of oxalic acid and thiobarbituric acids, which are potentially toxic chemicals. Therefore, this method is unsuitable for routine clinical analysis, particularly when rapid results are needed.

Separation of nonglycated hemoglobin from glycated hemoglobin by affinity chromatography capitalizes on the ability of boronates to form complexes with sugars. A suitable affinity column is prepared from a gel containing immobilized m-aminophenylboronic acid on cross-linked, beaded agarose. The boronic acid reacts with the cis-diol groups of glucose bound to hemoglobin to form a reversible 5-membered ring complex, thus selectively binding the glycated hemoglobin to the affinity column. The nonglycated hemoglobin passes through the column. The glycated hemoglobin is then dissociated from the complex by sorbitol. Although this method is less susceptible to variations in temperature or ionic conditions than other methods, such as colorimetry and ion-exchange chromatography, the affinity columns must be protected from sunlight and can only be reused a limited number of times before they must be discarded.

Antibody against Hb A1c can be prepared and used as the basis for a radioimmunoassay. However, such a radioimmunoassay, like radioimmunoassays in general, brings with it the problems of the disposal of reagents and the short shelf life of reagents due to degradation caused by radioactive labeling, with consequent loss of specific reactivity. Thus radioimmunoassay, though capable of accuracy, cannot generally be used for routine determinations of Hb A1c.

Ion exchange chromatography can be carried out using resins containing weakly acidic cation exchange or negatively charged carboxymethylcellulose resin. This procedure is time consuming and requires rigid control of temperatures of the reagents and the columns as well as the pH and the ionic strength. In practice, this means that the methods are usable only by highly skilled personnel and are not well suited to routine clinical determinations.

High performance liquid chromatography (HPLC) is a highly instrumental technique that is more costly initially, but is rapid, requires small samples, and can be automated. HPLC usually has great sensitivity and excellent reproducibility for the isolation of glycated hemoglobins. However, the accurate quantitation of Hb A1c by HPLC can be hampered when fetal hemoglobin, HbF, is present in elevated amounts.

Electrophoretic assays for Hb A1c or other glycoslyated proteins have given mixed results. Although Hb A1c is more negatively charged than Hb A$_0$, their isoelectric points differ by only 0.01 pH units. Consequently, modified methods like "mobile affinity electrophoresis", have been developed to magnify minor charge differences. Mobile affinity electrophoresis adds dextran sulfate to the buffers. This results in binding of sulfate groups to the nonglycated hemoglobins and acceleration of their electrophoretic mobilities. In another modified electrophoretic method, the fixed negative charge of the agar gel matrix can result in differential interaction with Hb $A_o$ and Hb A1c causing the separation of hemoglobins due to electroendoosmotic effects. Compared to mobile affinity electrophoresis, the agar gel method has given adequate, though less reproducible, results. A third electrophoretic method, Isoelectric focusing (IEF), provides definitive separation of glycated hemoglobins, unmatched by other charge dependent methods. However, the stability and reproducibility of the pH gradients required for this technique are tenuous at best. All electrophoretic methods developed to date require the skillful execution of numerous time consuming steps.

Each of these methods present problems of safety, accuracy, reproducibility, or efficiency. What is needed to overcome these problems is an assay that accurately and precisely distinguishes interaction with Hb $A_o$ and Hb $A_{1c}$ causing the separation of hemoglobins due to electroendoosmotic effects. Ideally, the assay is also rapid, efficient, uses inexpensive nontoxic reagents, has reusable equipment, and is amenable to automation for autosampling, on-line detection, and data acquisition.

SUMMARY

The present invention is directed to an assay that satisfies this need and a buffer for use in the assay. In particular, the buffer and the method can be used to determine the amount of glycosylated protein in a sample, and are particularly useful for determining the proportion of Hb A1c in a blood sample that contains other forms of hemoglobin.

The buffer comprises water, a sugar complexing compound, a zwitterionic compound that has a $pK_a$ of from about 9 to about 12, and sufficient base compound to adjust the pH of the buffer within the range of about 9 to 12. The sugar complexing compound can be boric acid, borax, sodium borate, or combinations of boric acid and sodium borate. The preferred molarity range of the sugar complexing compound is between about 50 mM and about 600 mM. A more preferable range is between about 200 mM and 400 mM, and the most preferred molarity is about 300 mM. In addition, the preferred molar ratio of the zwitterionic compound to the sugar complexing compound is from 1:10 to 1:1. Preferably the molarity range for the zwitterionic compound is between about 10 mM and about 200 mM, more preferably between about 50 mM and 150 mM, and most preferably about 100 mM. A preferred zwitterionic compound is 3-cyclohexylamino-1-propanesulfonic acid (CAPS). The pH range of the buffer is between about 9 and about 12, preferably greater than about 10, and most preferably about 11.

In a particularly preferred embodiment, the buffer comprises 300 mM sodium borate, 100 mM CAPS, and a sufficient amount of sodium hydroxide to bring the pH of the buffer to 11.

The capillary zone electrophoresis assay is accomplished by introducing a sample, comprised of a selected glycoprotein and the aforementioned buffer into a capillary tube. The tube is subjected to an electric field of sufficient voltage to allow separation of the selected glycoprotein from any of the other proteins in the sample. The electrophoretically separated proteins are detected by a suitable detection method, such as measurement of light absorption at 415 nm.

The assay can further comprise generating an electropherogram from a detection signal that is proportional to the quantity of proteins that are detected. The proportion of glycosylated protein to total protein can then be determined from the electropherogram.

Alternatively, the method can quantitate the amount of a selected glycosylated protein that is present in the sample. This quantitation requires the generation of a standard curve. A constant amount of an internal standard mixed with varying known amounts of protein are introduced into a capillary tube and subjected to capillary zone electrophoresis. Electropherograms of the mixtures are generated from a detection signal that is proportional to the amount of internal standard and protein. The ratio of the internal standard to the protein concentration is plotted versus the ratio of the internal standard signal to the protein signal. A sample comprising the glycoprotein mixed with a known amount of internal standard is then subjected to capillary zone electrophoresis thereby separating the glycoprotein from the internal standard. The ratio of the internal standard signal to the glycoprotein signal is determined from the electropherogram. This ratio can then be compared to the standard curve and used to calculate the amount of glycoprotein present in the sample.

DRAWINGS

These and other features, aspects, and advantages of the present invention will become better understood with regard to the following description, appended claims, and accompanying drawings where:

DESCRIPTION

Figure 1:
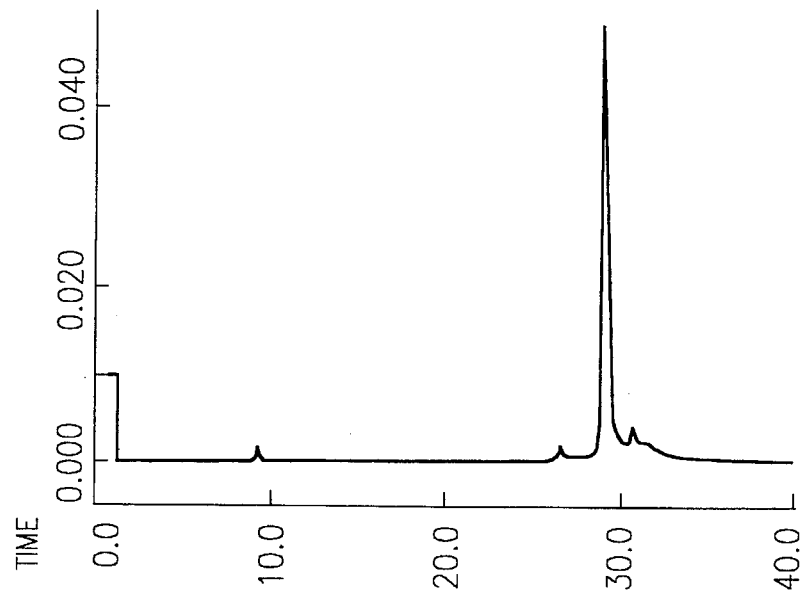
FIG. 1 is an electropherogram of a sample that contained 7.1% Hb A1c, as determined by the present invention.

Capillary zone electrophoresis is a technique that employs narrow-bore (10–200 µm inside diameter) capillaries to perform high efficiency separations of macromolecules. This separation is attained by the use of high voltages, typically 1,000 to 30,000 volts, which can generate electroosmotic and electrophoretic flow of buffer solutions and ionic species, within the capillary.

Electroosmosis is a consequence of the surface charge on the wall of the capillary. The fused silica capillaries that are typically used for separations have ionizable silanol groups in contact with the buffer contained within the capillary. The degree of ionization is controlled mainly by the buffer. Since the pI of fused silica is about 1.5, most buffers with a pH of greater than 1.5 can ionize the capillary wall. The negatively charged wall attracts positively charged ions from the buffer, creating an electrical double layer. A rigid double layer of adsorbed ions is superposed by a diffuse double layer. This double layer system causes an electric potential across the rigid double layer as well as across the diffuse double layer. The latter is known as the zeta potential. When a voltage is applied across the capillary, cations in the diffuse portion of the double layer migrate in the direction of the cathode carrying water with them. The result is an electroosmotic flow (EOF) that causes liquid transport toward the negative electrode in a manner analogous to a mechanical pump.

On the other hand, electrophoretic migration is dependent on the charge-mass ratio of the macromolecule, e.g., protein, to be separated. Each molecule possesses a specific charge-mass ratio depending upon its size and amino acid composition and thus migrates with a different speed. Negatively charged analytes, such as proteins, peptides, or other species, in the buffer solution move against the EOF by electrophoretic migration towards the positive electrodes. Despite the electrophoretic migration of the analytes towards the positive electrode (anode), the pump-like action of EOF overwhelms the electrophoretic migration of the analytes, and the analytes are pushed back toward the negative electrode (cathode).

A. The Buffer

The selection of an appropriate buffer for capillary zone electrophoresis is critical for the differentiation of closely related protein species. The buffer of the present invention has at least four elements that facilitate the separation of glycoproteins such as Hb A1c from other sample constituents. These include water, a sugar complexing compound, a zwitterionic compound that has a $pK_a$ of from about 9 to about 12, and a base compound for adjusting the pH.

The first consideration for an effective capillary electrophoresis buffer is the choice of an effective pH range. The pH of the present invention's buffer is greater than the pI values for substantially all the constituent species in the sample being analyzed. This ensures that all sample constituents have the required net negative charge. A net negative charge facilitates the separation of hemoglobin variants because such negatively charged species resist traveling towards a cathode under the influence of the electroosmotic flow of the bulk solution. For clinical samples, this requires a pH greater than about 8. At a pH of about 8.6, all hemoglobin species have a net negative charge. Consequently, the pH of applicants' buffer is adjusted with a base compound to preferably at least about 9, but is kept below about 12 to avoid protein degradation. More preferably, the pH is at least about 10 and in the most preferred embodiment the pH is about 11. Preferred base compounds are sodium hydroxide and potassium hydroxide.

Borate compounds have proven particularly useful in capillary electrophoresis buffers over the preferred pH range of about 9 to about 12. In addition to providing sufficient buffering capacity and low conductivity, borates form stable complexes with sugar residues on glycoproteins. Borate complexes add a negative charge to the glycoprotein. The magnitude of the negative charge is determined by the stability of the complex. Consequently, the electrophoretic mobility of the glycoprotein is modified, eluting as a later peak than an unmodified protein counterpart. Since compilation of sugar moieties with borate is strongly dependent on the buffer pH and the borate concentration, both parameters can be adjusted for optimization of the separation such that higher pH and higher borate concentration result in a higher proportion of the complexed species and in a more negative net charge. For the present invention, applicants have determined that a buffer comprised of boric acid, borax, or sodium borate present in an amount of from 50 mM to 600 mM is preferable, and from 200 mM to 400 mM is even more preferable, for the stable formation of negatively charged borate-Hb A1c complexes. At higher concentrations of borate increased conductivity and Joule heating may hinder resolution.

CAPS (3 [cyclohexylamino]-1-propane sulfonic acid) is another compound that has proven useful over the preferred pH range of the present invention's buffer. CAPS is a zwitterion with a pKa value between 10 and 11. Within the pH range of about 9 to 12, the net charge of the compound is close to zero. The addition of CAPS to the buffer increases the ionic strength and the viscosity of the buffer without increasing the current during separation in the capillary. A concomitant increase in the resolution of hemoglobin A1c from other hemoglobin variants occurs when the present invention's buffer includes CAPS in an amount of about 10 mM to 200 mM, and preferably about 50 mM to 150 mM.

The optimum buffer has been determined to contain sodium borate in an amount of about 300 mM, CAPS in an amount of about 100 mM, and sufficient sodium hydroxide so that the buffer has a pH of about 11.

B. The Method

CZE analysis usually involves dilution of the sample being analyzed. For example, serum, plasma, and whole blood are diluted prior to introduction to the capillary in order to assist these samples in flowing through the capillary; urine and cerebrospinal fluid can be diluted, but dilution is not a requirement. Dilution is typically from about 1 part sample to about 20 parts diluent (1:20=0.05) to about 1:100 (0.01). If hemoglobin from whole blood samples is to be detected at wavelengths that detect substantially all proteins, plasma proteins are first removed from red blood cells before hemolysis.

The process of capillary electrophoresis can be carried out in any apparatus in which the suitable electrophoretic forces can be generated and in which the peaks resulting can be detected. Typically, the capillary electrophoresis system involves a quartz or fused silica capillary tube of circular cross-section and cylindrical outline. Typical dimensions of the capillary tube are 25 µm inner diameter×27 cm total length. A suitable capillary tube is that produced by Polymicro Technologies, Phoenix, Ariz. The outer surface of the capillary can be coated with polyimide to protect the capillary from breakage.

The capillary is filled with buffer solution and placed between two buffer reservoirs. Sample injection is performed by a hydrodynamic injection method, wherein a pressure drop is applied along the capillary either by high pressure at the injection side, vacuum at the detector side, or hydrostatic pressure using gravity. Electrokinetic injection is unsuitable for quantitation of hemoglobin A1c because it discriminates among ionic species. An electric field of up to 500 volts per centimeter of capillary tube is applied by means of a high voltage power supply.

An on-column detector comprised of an ultraviolet emitter (deuterium lamp) and monochromator to select the desired wavelength, as well as a photodetector to detect the ultraviolet light that has passed through the sample, is located at the end of the capillary which is opposite to the injection site. Preferably, the signal detected is proportional to the quantity of the macromolecules under investigation. The plot of the detector response versus the migration time is called an electropherogram. A computer connected to the detector allows data acquisition and interpretation.

A suitable apparatus for detection of proteins based on ultraviolet absorbance is the Beckman Instruments PlACE™ CE systems (Beckman Instruments, Fullerton, Calif.). This system is computer controlled and can be used with suitable software, such as the CCE software, and an IBM-compatible personal computer such as an IBM PS/2. Other suitable capillary electrophoresis apparatus can also be used.

Although the detected signal has been described for particular wavelengths, in particular 415 nanometers, for the detection of hemeproteins such as hemoglobin, it is apparent that the electrophoresis system could operate at many different wavelengths. Other examples of suitable wavelengths are 214 nanometers for the detection of peptide bonds or 280 nanometers for the detection of aromatic amino acid residues. Signals at multiple discrete wavelengths can be applied to one or more detection paths intersecting the tube.

C. Quantitation

Quantitative analysis is typically performed by determination of peak areas from the electropherogram. A suitable data analysis system, such as Beckman CCE software (Beckman Instruments, Inc., Fullerton, Calif. USA.) integrates the product of the detection signal and the corresponding time interval to determine the peak area.

For one embodiment of the present invention, the peak area of the glycated hemoglobin, Hb A1c, is compared with the cumulative total of all the peak areas to give a value representing the percentage of Hb A1c to total hemoglobin.

In another embodiment of the present invention an internal standard is used to calculate the absolute concentration of Hb A1c in a sample. This is carried out by adding a known substance (internal standard) to reference solutions with defined concentrations of protein. The internal standard compound produces a signal in relation to its concentration and is capable of electrophoretic separation from all other components in the reference solution or the sample. By plotting the peak ratios versus the concentration ratios a standard curve can be obtained from which the concentration of the sample can be calculated.

Determining the concentration of sample component(s) is carried out by adding a known quantity of an internal standard compound to the sample. The electropherogram representing the signal produced by the internal standard compound is then measured and compared to the signal produced by the sample component(s) to determine a ratio of peak areas. The absolute concentration of the sample component(s) is then determined from a standard curve of peak area ratios versus the ratios of internal standard concentration to protein concentration.

An alternative method for determining the absolute concentration of sample component(s) involves plotting a standard curve of peak areas using reference solutions (external standards) with known protein concentrations. Subsequently, a sample is injected and the peak area is determined in the same way as the reference solutions. This external reference method requires highly accurate and reproducible injection volumes for comparing peak areas between consecutive runs. Consequently, the previously described internal standard method is generally the method of choice for quantitative analysis.

The present invention represents an improvement over previous reagents and methods. The buffer is economical, effective, and nontoxic. The combination of a sugar complexing compound with a zwitterionic compound that has a $pK_a$ of from about 9 to about 12 assures the separation of glycoproteins, such as Hb A1c, from closely related macromolecules. The capillary electrophoresis method is rapid, reliable, and efficient. It is amenable to automation, such as autosampling, on-line detection and data acquisition, which facilitates the accurate quantitation of glycoproteins, such as Hb A1c.

EXAMPLES

The proportion of hemoglobin A1c (Hb A1c) to hemoglobin A (Hb A) was determined for 30 blood specimens using the present invention. This example shows that the present invention gives quantitative results for HbA1c that are comparable to previous methods.

A. Sample Preparation

Red blood cells in specimens from normal and diabetic patients were allowed to settle at room temperature, plasma were removed, and packed cells were collected. Alternatively, red blood cells were collected after a brief centrifugation step. Red blood cells were hemolyzed with tris/maleic acid/triton X-100 or distilled water at a sample/hemolyzing reagent ratio of 1:20(v/v). Hemolysate was centrifuged to remove cell debris before subjecting the sample to capillary electrophoresis.

B. Apparatus

A Beckman P/ACE™ 2100 CE System was used with Beckman CCE software, which is controlled by an IBM PS/2. Electrophoresis was performed in an untreated fused silica capillary tube. The outer surface of the capillary was coated with polyimide to protect the capillary from breakage (Polymicro Technologies, Inc., Phoenix, Ariz.). The optic module and detector included a UV light source (deuterium lamp) and a 415 nanometer filter in a rotating wheel, as well as a detector that aligned with the aperture of the window. The window was located at 6.5 cm from the tube outlet.

C. Capillary Electrophoresis Reagents

Running buffer was prepared as follows: 18.55 g of boric acid and 22.13 g of 3-cyclohexylamino-1-propanesulfonic acid (CAPS) were dissolved in 800ml of distilled water. A pH meter was calibrated with two standard pH solutions at pH 7.0 and 10.0, and the boric acid/CAPS solution was then adjusted to a pH of 11.0 with 1N NaOH. The boric acid/CAPS solution was then adjusted to a final volume of 1000 ml using a volumetric apparatus, filtered through a 0.22 μm membrane (Corning, Corning, N.Y., Filter Catalog Number 25952), and stored at room temperature in a glass bottle.

Rinse solution A was 1 N NaOH. Rinse solution B was deionized water.

D. Procedure for Capillary Electrophoresis

The parameters for electrophoresis were set as follows: The capillary was 25 μm ×27 cm, with a separation length of 20 cm. The wavelength for measurement was 415 nm. The temperature was 24° C. The injection mode was pressure injection at 0.5 psi (positive) for 10 seconds. The separation voltage was 5 kV (185 volts/cm). The separation time was 40 minutes. The current was 22.4 μAmp.

The operating sequence was set as follows: The column was rinsed with running buffer for 1.5 minutes. The column was equilibrated with running buffer for 0.5 minutes. Pressure injection was performed for ten seconds as indicated, and the separation was performed at 5 kilovolts for 40 minutes. The column was then rinsed with rinse solution A for 1 minute, and then with rinse solution B for 1 minute.

Column maintenance was as follows: At the beginning of each day, the column was rinsed with rinse solution A for 1 minute, rinse solution B for 5 minutes, and running buffer for 15 minutes. At the end of each day, the column was rinsed with rinse solution A for 1 minute and rinse solution B for 5 minutes.

For data analysis, the CCE software (Beckman Instruments, Fullerton, Calif.) was used to adjust the baseline. The "delimit" integrator function was then used to calculate the relative area under the peaks and the required ratios of the peak areas.

Figure 2:
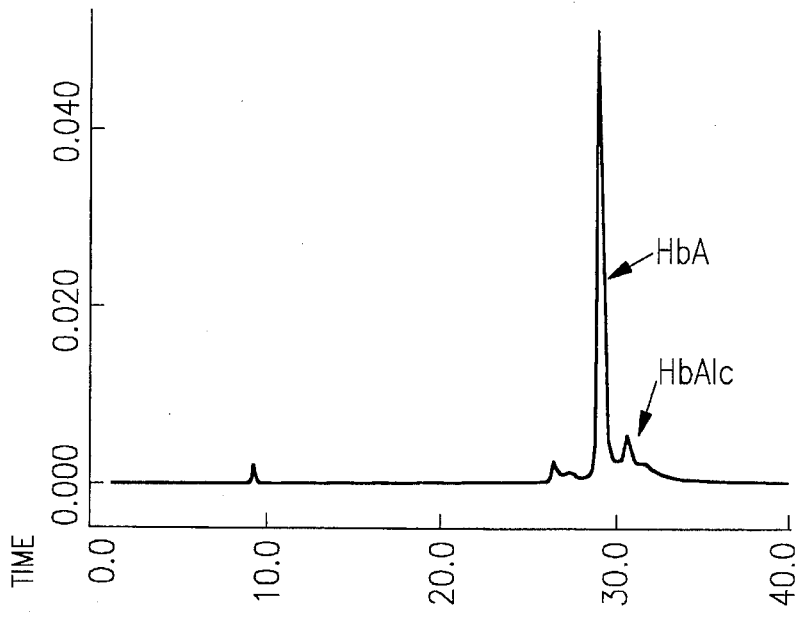
FIG. 2 is an electropherogram of a sample that contained 10% Hb A1c, as determined by the present invention.
Figure 3:
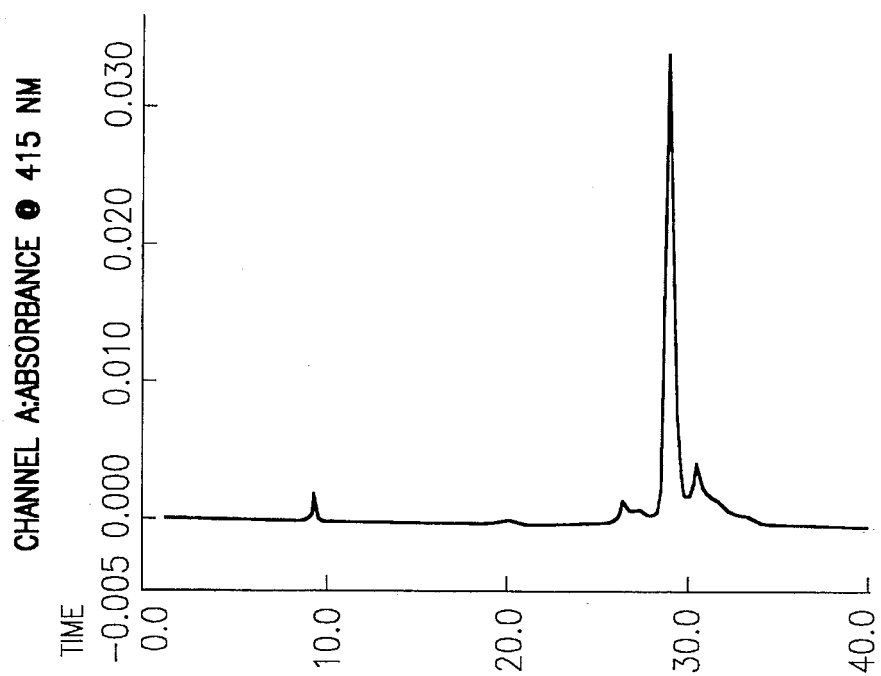
FIG. 3 is an electropherogram of a sample that contained 11.8% Hb A1c, as determined by the present invention.
Figure 4:
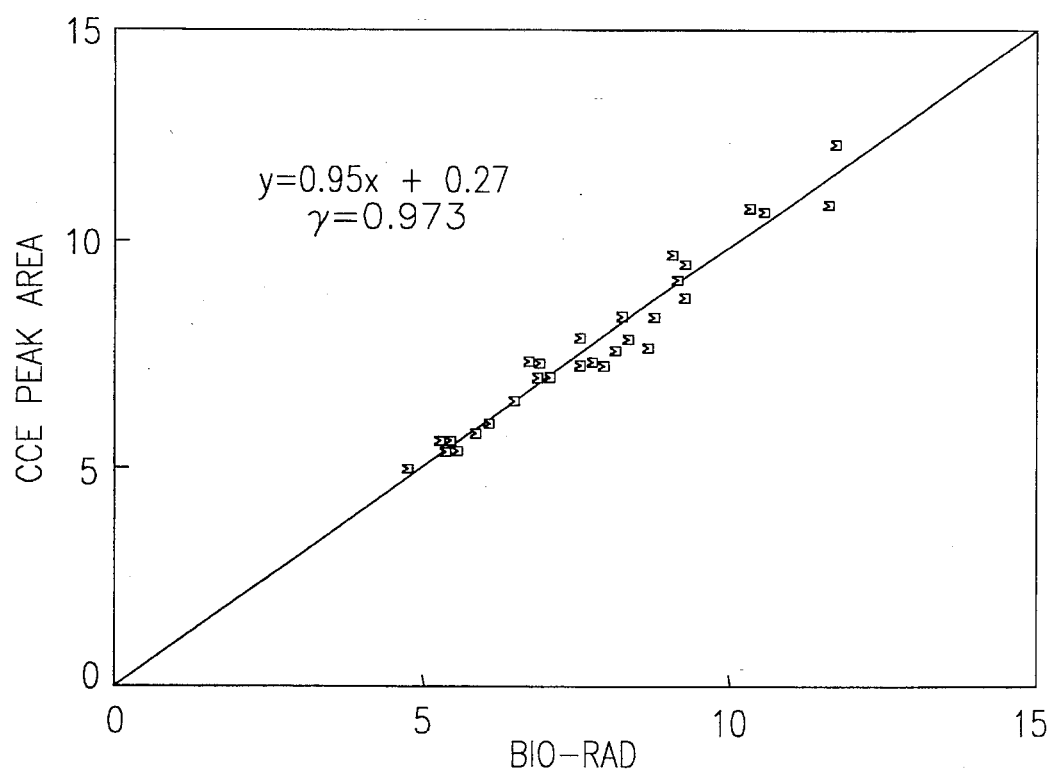
FIG. 4 is a plot of a linear regression analysis, which compares the quantitation of Hb A1c by the present invention versus the Bio-Rad ion exchange HPLC method.

FIGS. 1, 2, and 3 are electropherograms at 415 nm, which monitors the heme moiety of the analyte. In FIG. 2 the Hb A1c is indicated by an arrow. Integration of the peak areas in FIGS. 1, 2 and 3 reveals that the Hb A1c peaks represent about 7.1%, 10%, and 11.8%, respectively, of the total hemoglobin in the samples. By comparison, the Bio-Rad ion exchange HPLC method gave values of 7.4%, 9.8%, and 12% Hb A1c for FIGS. 1, 2 and 3, respectively. Comparison data for all thirty samples are shown in Table 1. Linear regression analysis of these data showed a slope of 0.98, an intercept of 0.27 and a correlation coefficient of 0.973 between the two methods. Thus, the CE method described in this invention is equivalent to a conventional ion-exchange method, such as Bio-Rad's HPLC method.

| SAMPLE # | BIO-RAD | CCE |
| --- | --- | --- |
| 1 | 5.50 | 5.48 |
| 2 | 4.70 | 5.04 |
| 3 | 5.20 | 5.69 |
| 4 | 5.30 | 5.45 |
| 5 | 5.40 | 5.68 |
| 6 | 5.80 | 5.87 |
| 7 | 6.00 | 6.07 |
| 8 | 6.40 | 6.56 |
| 9 | 6.70 | 7.46 |
| 10 | 6.80 | 7.44 |
| 11 | 7.50 | 7.38 |
| 12 | 7.70 | 7.44 |
| 13 | 7.00 | 7.10 |
| 14 | 7.50 | 7.97 |
| 15 | 7.90 | 7.37 |
| 16 | 8.20 | 8.38 |
| 17 | 8.30 | 7.97 |
| 18 | 8.10 | 7.67 |
| 19 | 8.20 | 8.47 |
| 20 | 8.60 | 7.76 |
| 21 | 8.70 | 8.44 |
| 22 | 9.00 | 9.87 |
| 23 | 9.10 | 9.27 |
| 24 | 9.20 | 9.63 |
| 25 | 9.20 | 8.85 |
| 26 | 10.50 | 10.87 |
| 27 | 10.30 | 10.94 |
| 28 | 11.60 | 11.03 |
| 29 | 11.70 | 12.47 |
| 30 | 6.80 | 7.08 |

Although the present invention has been described in considerable detail with reference to certain preferred versions, other versions are possible. For example, other glycoproteins may be separated from their nonglycosylated counterparts using the present invention's buffer and method. In addition, quantitation of proteins may be accomplished by a method that does not require the intermediate step of generating an electropherogram. Therefore, the spirit and scope of the appended claims should not be limited to the description of the preferred versions contained herein.

What is claimed is:

1. A buffer composition suitable for capillary electrophoresis detection of a glycated hemoglobin, the buffer composition formed by combining:
   (a) water;
   (b) a sugar complexing compound capable of complexing with sugar moieties of glycoproteins, the sugar complexing compound being present in an amount of from about 50 mM to about 600 mM;
   (c) sufficient base compound that the pH of the buffer composition is from about 9 to about 12; and
   (d) a zwitterionic buffer compound that has a $pK_a$ of from about 9 to about 12, in a molar ratio to the sugar complexing compound of from 1:10 to 1:1.

2. A buffer composition as in claim 1 wherein the sugar complexing compound is selected from the group consisting of boric acid, borax, and combinations of boric acid and borax.

3. A buffer composition as in claim 2 wherein the sugar complexing compound is boric acid in an amount of from about 200 mM to 400 mM.

4. A buffer composition as in claim 3 wherein the concentration of boric acid is about 300 mM.

5. A buffer composition as in claim 1 wherein the sugar complexing compound is sodium borate in an amount between about 200 mM to 400 mM.

6. A buffer composition as in claim 5 wherein the concentration of sodium borate is about 300 mM.

7. A buffer composition as in claim 1 wherein the base compound is potassium hydroxide.

8. A buffer composition as in claim 1 wherein the base compound is sodium hydroxide.

9. A buffer composition as in claim 1 wherein the pH of the buffer is greater than about 10.

10. A buffer composition as in claim 9 wherein the pH of the buffer is about 11.

11. A buffer composition as in claim 1 wherein the zwitterionic buffer compound is 3-cyclohexylamino-1-propanesulfonic acid (CAPS) in an amount between about 10 mM and about 200 mM.

12. A buffer composition as in claim 11 wherein the concentration of CAPS is between about 50 mM and about 150 mM.

13. A buffer composition as in claim 12 wherein the concentration of CAPS is about 100 mM.

14. A buffer composition suitable for electrophoretic separation of hemoglobin (Hb) A1c from other Hb's, the buffer composition being formed by combining:
   (a) water;
   (b) a sugar complexing compound selected from the group consisting of boric acid, sodium borate, borax, and combinations of boric acid and sodium borate in an amount of from about 50 mM to about 600 mM;
   (c) sufficient base compound that the pH of the buffer is between about 10 and about 12; and
   (d) 3-cyclohexylamino-1-propanesulfonic acid (CAPS) in an amount between about 10 mM and about 200 mM.

15. A buffer composition suitable for capillary electrophoresis separation of hemoglobin (Hb) A1c from at least one other form of hemoglobin, the buffer comprising:
   (a) water;
   (b) sodium borate in an amount of about 300 mM;
   (c) sufficient NaOH that the pH of the buffer is about 11; and
   (d) 3-cyclohexylamino-1-propanesulfonic acid (CAPS) in an amount of about 100 mM.

16. A method for detecting a selected glycoprotein by capillary zone electrophoresis comprising the steps of:
   (a) introducing into a capillary tube a sample comprising the selected glycoprotein, and the buffer composition of any one of claims 1, 14, or 15;
   (b) applying an electric field of sufficient voltage to the capillary tube to allow separation of the selected glycoprotein from any other proteins which may be present in the sample; and (c) detecting the selected glycoprotein present in the sample.

17. The method of claim 16 wherein the glycoprotein is glycated hemoglobin.

18. The method of claim 17 wherein the glycated hemoglobin is Hb A1c.

19. The method of claim 16 further comprising the steps of:
   (d) generating an electropherogram from a detection signal that is proportional to the quantity of protein detected; and
   (e) determining the ratio of the selected glycoprotein to total protein in the sample from the electropherogram.

20. A method according to claim 19 wherein the selected glycoprotein is a glycated hemoglobin.

21. A method according to claim 20 wherein the glycated hemoglobin is Hb A1c.

22. An assay for quantitating the amount of a selected glycoprotein by capillary zone electrophoresis comprising the steps of:
   (a) generating a standard curve comprising the steps of:
      i) forming mixtures comprising a constant amount of an internal standard and varying amounts of protein, the internal standard compound being separable from the protein;
      ii) introducing the mixtures into a capillary tube containing the buffer composition of claim 1;
      iii) subjecting the mixtures to capillary electrophoresis;
      iv) generating electropherograms from a signal proportional to the quantity of internal standard and the quantity of protein; and
      v) plotting the ratio of the internal standard:protein concentration versus the ratio of the internal standard signal:protein signal;
   (b) introducing into a capillary tube a sample comprising the selected glycoprotein, a known amount of internal standard, and the buffer composition of claim 1, the internal standard compound being separable from the glycoprotein;
   (c) subjecting the sample to capillary electrophoresis to generate an electropherogram;
   (d) determining the ratio of the internal standard signal: selected glycoprotein signal from the electropherogram; and
   (e) determining the amount of glycoprotein present in the sample from the standard curve.

23. An assay according to claim 22 wherein the selected glycoprotein is a glycated hemoglobin.

24. An assay according to claim 23 wherein the glycated hemoglobin is Hb A1c.

\* \* \* \* \*